United States Patent [19]

Boebel

[11] Patent Number: 5,354,313
[45] Date of Patent: Oct. 11, 1994

[54] FORCEPS HAVING ADJUSTABLE GRIPPING FORCE

[75] Inventor: Manfred Boebel, Oetisheim, Fed. Rep. of Germany

[73] Assignee: Richard Wolf GmbH, Knittlingen, Fed. Rep. of Germany

[21] Appl. No.: 65,628

[22] Filed: May 21, 1993

[30] Foreign Application Priority Data

May 22, 1992 [DE] Fed. Rep. of Germany ....... 4216971

[51] Int. Cl.$^5$ ............................................. A61B 17/28
[52] U.S. Cl. .................................... 606/208; 606/206
[58] Field of Search ............. 606/205, 206, 208, 210, 606/142, 143; 294/100, 16, 115

[56] References Cited

U.S. PATENT DOCUMENTS

| | | | |
|---|---|---|---|
| 1,350,675 | 8/1920 | Smith | 294/115 |
| 4,602,631 | 7/1986 | Funatsu | 606/142 |
| 4,968,078 | 11/1990 | Fitzwater | 294/16 |
| 5,222,973 | 6/1993 | Sharpe et al. | 606/206 |

FOREIGN PATENT DOCUMENTS

| | | |
|---|---|---|
| 418761 | 3/1991 | European Pat. Off. ........... 606/206 |
| 0450608 | 10/1991 | European Pat. Off. . |
| 3601166 | 7/1987 | Fed. Rep. of Germany . |
| 8813678 | 2/1989 | Fed. Rep. of Germany . |
| 3931577 | 4/1991 | Fed. Rep. of Germany . |

OTHER PUBLICATIONS

Copies from Duden, Band 5, "Das Fremdwörterbuch", 4. Auflage, 1992–pp. 192 and 633.

Primary Examiner—Tamara L. Graysay
Attorney, Agent, or Firm—Cohen, Pontani, Lieberman, Pavane

[57] ABSTRACT

Forceps suitable for gripping body tissue or organs including a pair of jaws the gripping force of which can be adjusted. The forceps include an operating rod providing with axially spaced angularly offset cams which are selectively engagable by rotating the control rod with longitudinally slidable link assemblies separated by compression springs of differing stiffnesses. Rotation of the control rod to a particular angular position determines whether no spring or one or more springs are connected in series to determine the gripping force exerted by the forceps when the control rod is axially displaced. A control rod actuating lever is locked in position by means of a locking device.

15 Claims, 2 Drawing Sheets

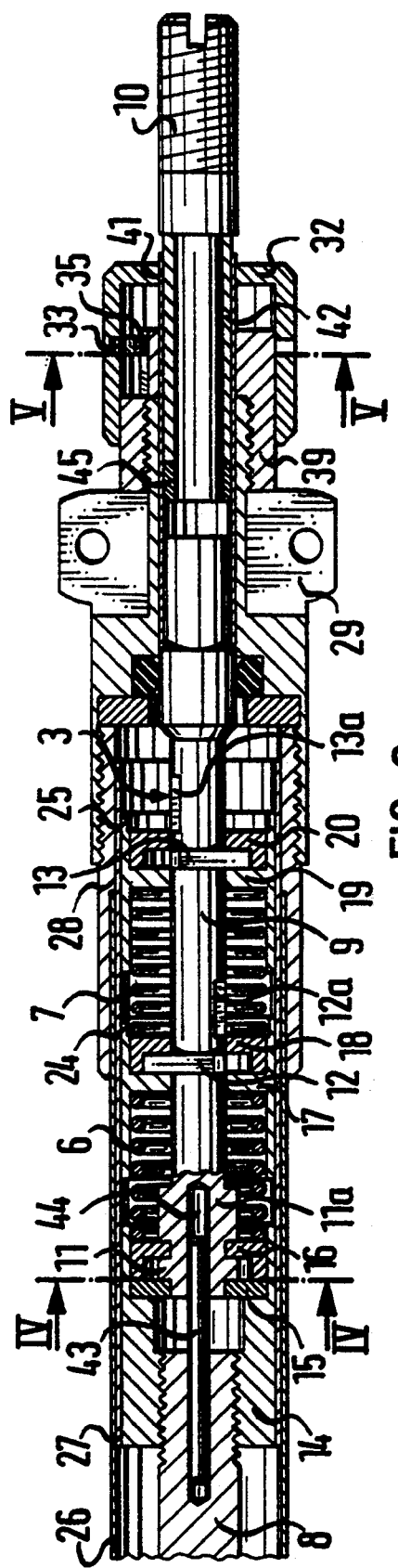
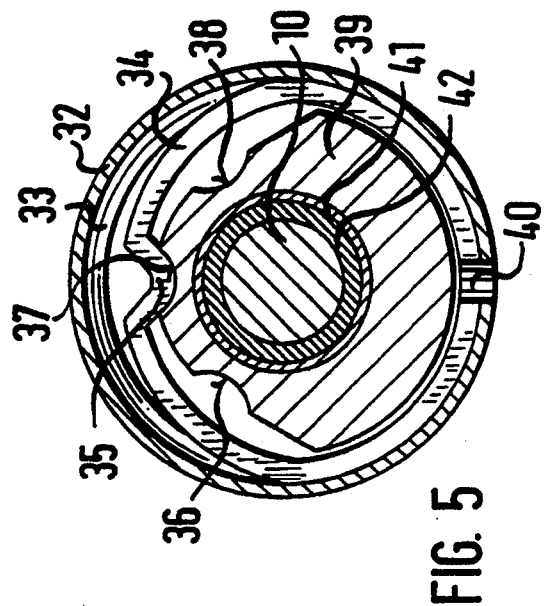
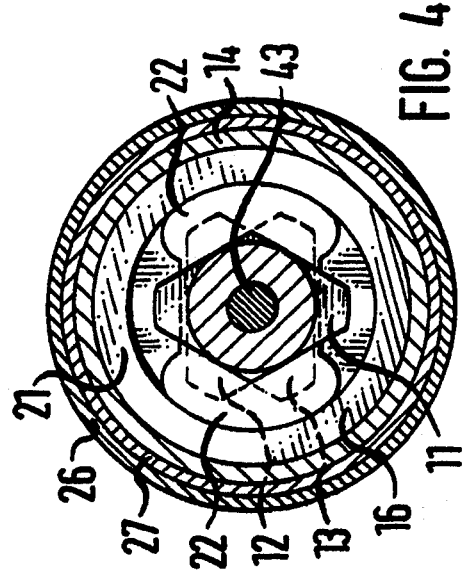

FORCEPS HAVING ADJUSTABLE GRIPPING FORCE

TECHNICAL FIELD

The invention relates to forceps with gripping jaws for gripping body tissue, body organs or the like, in which at least one jaw is pivotable relative to the other by adjustment of an operating rod actuated by a lever, and more particularly to forceps in which the jaws and the lever can be fixed by a locking device in a closed position.

BACKGROUND ART

Forceps of this type must be designed in such a way that they can hold tissue absolutely reliably. Patent DE3931577A discloses forceps for binding tissue sections together. The forceps guarantee a reliable fixing of the gripped tissue by means of a specially developed stop mechanism which clicks securely into position after pressure on a first pressure point overcomes a threshold to hold the forceps securely closed. The release of the forceps is effected by applying pressure to a further pressure point.

It is undesirable if such forceps traumatise the gripped tissue, particularly if the gripped tissue becomes detached from the body. When organs or tissue parts which need to fulfil their task in the body have to be fixed or gripped for manipulation, traumatisation is particularly undesirable. In such a situation a soft and non-traumatic grip of the tissue or organ must be effected.

In the prior art forceps it is possible to provide a gentle gripping force by means of the force applied to a gripping actuation mechanism. The disadvantage of such an arrangement is that a fixing of the clamped jaw position with a stop mechanism is not possible and thus not reliable and secure holding of the tissue can be guaranteed.

OBJECTS OF THE INVENTION

Accordingly, an object of the invention is to provide forceps in which the closing force acting on the tissue or the like present between the jaws of the forceps can be altered and set in order to prevent traumatisation of the tissue. A further object of the invention is to provide forceps which meet all the aforementioned requirements, in particular with regard to absolutely reliable operation.

SUMMARY OF THE INVENTION

Thus, according to the invention there is provided a pair of forceps of the type discussed above, in which the gripping force of the jaws is adjustable to different values. The forceps can be fixed in a closed position by a locking device, and in addition, different closing forces can be set, so that tissue gripped by the forceps is not traumatised.

Preferably the forceps are so designed that the force exerted via the lever and the operating rods is transferred directly to the jaws by setting the maximum closing power, and is transferred indirectly via at least one spring by setting a different lower closing power. With such an arrangement, the forceps can be set to maximum gripping force for gripping tissue when it is unimportant whether the tissue is traumatised and be set to a lower gripping force when used for gripping tissue which should in no way be traumatised.

The operating rod of the forceps consists of a distal first rod part connected to the movable jaws and a second rod part extending proximally from the distal rod part. For the purpose of setting the different gripping forces, the second rod part can be turned about its axis in relation to the first and is provided with axially spaced angularly offset cams. These cams co-operate with link assemblies so that for a given angular orientation of the second rod part only the cams required for a desired gripping force are engaged. The gripping force can be transferred from the second to the first rod parts either directly, or indirectly via springs depending on which of the cams is engaged with associated link assemblies. It is understood that the number of components such as cams, link assemblies and springs connected in series depends on the number of closing force settings required.

Apertures are provided in the link assemblies which ensure free axial passage of the cams in certain angular orientations of the second rod part. In addition, the compression springs located between adjacent link assemblies urge the link assemblies against stops or ring shoulders. Such stops secure the link assemblies in the rest position against movement in the proximal direction.

Furthermore, the operating rod has a switching ring on its proximal end. This ring is fitted with a spring possessing an inwardly directed lug and can be turned in relation to a stationary part of the forceps. The lug is selectively engagable with one of several orifices on the aforementioned stationary part and thus permits selective fixing of the angular position of the second rod part so as to regulate the jaw gripping force provided. The turnable spring can be fitted in such a way that it is engaged by a peg and is fixed into the switching ring. This arrangement prevents jamming and/or turning of the spring which is located within a circular notch in the switching ring. By this arrangement the proximal rod part can be fixed in three discrete angular positions.

The transfer of the turning movement of the switching ring to the proximal rod part is achieved by means of a cylindrical casing. The first distal and second rod parts are preferably axially displaceable with respect to each other, being connected by means of a pin which secures these rod parts against radial movement relative to each other.

BRIEF DESCRIPTION OF THE DRAWINGS

The above and other objects of the invention will become apparent from the following description of the accompanying Figures which show.

DETAILED DESCRIPTION

Figure 1:
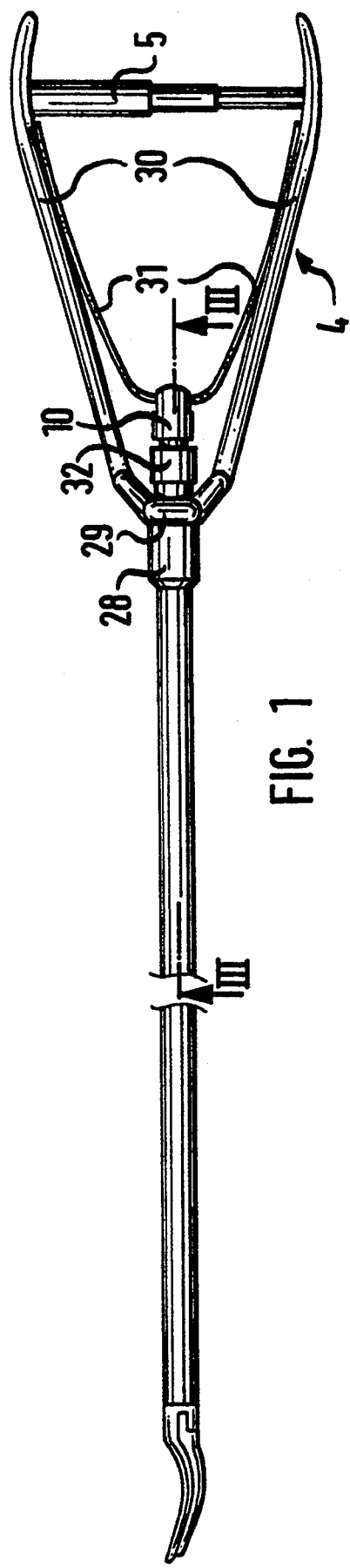
FIG. 1 a side view of the forceps according to the invention
Figure 2:
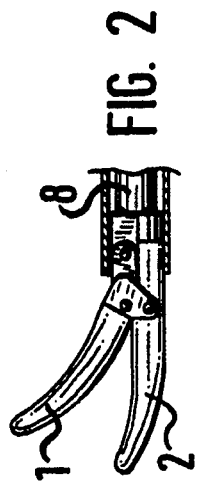
FIG. 2 a partial longitudinal section through the distal end region of the forceps with the jaws in the open position FIG. 3 a section on the on the line III—III through the proximal end of the forceps according to FIG. 1 shown on a larger scale and showing a device for adjusting the gripping force FIG. 4 a section on the line IV—IV of FIG. 3 on an enlarged scale and FIG. 5 a section on the line V—V of FIG. 3 on an enlarged scale.

The forceps shown in the Figures have a pair of jaws 1 and 2 for gripping and holding tissue at their distal end. An operating rod 3 comprising first second and third parts 8, 9 and 10 extends from the distal end of the forceps to a handle 4 with an integrated stop mechanism or locking device 5 at the proximal end. The mechanism 5 is used to determine the closing position of the jaws 1 and 2. One jaw 1 is pivotable in relation to the other 2 by axially displacing the operating rod 3 by means of the handle 4.

The gripping force transferable to the jaw 1 by means of the operating rod 3 can be adjusted for example to three defined levels. FIG. 3 shows the internal components for changing the gripping force.

Two compression springs 6 and 7 and are provided which transfer the force exerted by the handle 4 to the first part 8 of the operating rod 3, and thus to the movable jaw 1. The springs 6 and 7 are employed selectively for the two lower gripping force settings. Should the maximum closing force be required the force exerted by the handle 4 is transmitted directly to the first part 8 of the operating rod 3 i.e. without any intermediary springs.

The operating rod 3 consists of a first rod part 8 a second central rod part 9 extending proximally from the first part 8 and a third rod part 10 at a proximal end of the forceps. The first rod part 8 is connected directly to the pivotable jaw 1, for example by a linkage. The second rod part 9 is turnable about its axis in relation to the first rod part 8. Furthermore, the second rod part 9 is fitted with cams 11, 12 and 13 arranged axially spaced from one another, and angularly displaced with respect to one another. These cams co-operate with axially movable link assemblies 14, 15, 16, 17, 18, 19 and 20. Distal cam 11 is co-operable with distal link assembly 14, 15, 16, middle cam 12 is co-operable with middle link assembly 17, 18, and proximal cam 13 is co-operable with proximal link assembly 19, 20. Each link assembly includes a sleeve 14, 17, 19 and one or more apertured plate 15, 16, 18 and 20. These plates and inwardly projecting flanges 21 of the sleeves 17 and 19 each include a pair of opposed arcuate apertures 22 as shown in FIG. 4. The apertures of each link assembly are configured so as to restrain the associated cam against longitudinal movement relative thereto in either direction as shown in solid lines in FIG. 4, or allow longitudinal movement relative thereto as shown in dotted lines in FIG. 4 (by the passage of cams through their associated apertures). The cams 11, 12, 13 and apertures 22 in the link assemblies are angularly positioned so that in each of three discrete angular positions of the operating rod 3, only one of the cams is restrained by its associated link assembly as described above.

Should the maximum closing force be required, the second rod part 9 is swivelled to the position shown in FIG. 4. Only the distal cam 11 is engaged with the distal link assembly 14, 15 and 16. The force exerted on the proximally extending second and third rod parts 9 and 10 is transferred via the distal link assembly 14, 15 and 16 to the first rod part 8. The middle cam 12 and proximal cam 13 can freely traverse the associated middle link assembly 17, 18 and proximal link assembly 19, 20 respectively, unimpeded.

The compression springs 6 and 7 urge the link assemblies against circular shoulders 24 and 25 such that the circular shoulders 24 and 25 secure the link assemblies in the rest position against proximal movement. The circular shoulders 24, 25 are arranged in the device in such a way that they are fixed immovably in a cylindrical casing 27 fitted coaxially in an outer handle 26. Outer handle 26 fits inside a housing part 28, which is connected to the proximal housing part 29 by a screw connection. Two levers 30 constituting the handle 4 are pivotably fixed to the proximal end of the housing part 29.

Between the levers 30 a return spring 31 is provided. Compressing the levers 30 transfers power from the levers 30 to the proximal rod part 10, so as to move the rod parts 8, 9 and 10 distally. Moreover, the return spring 31 automatically returns the levers 30 and the operating rod 3 to the starting position after releasing the locking device 5.

FIG. 5 shows a cross section on the line V—V through a switching ring 32 formed by a hollow cylinder which is rotatable by hand and provided on the proximal rod part 10 in order to set the different gripping forces, by defining three discrete rotational positions for the rod part 9. The switching ring 32 has a circular spring 34 received in a circumferentially extending notch 33 thereof and secured therein against circumferential movement relative to the ring 32 by a peg 40. The ring 32 and the spring 33 are jointly turnable in relation to a fixed part 39. An inwardly directed cam 35 on the spring 34 engages in one of the orifices 36, 37 or 38 provided on the fixed part 39 according to the gripping force to be set. By means of this design, different settings can be achieved and more securely effected, since the actual position of the rod part 9 is felt by clicking of the cam 35 into position in one of the orifices 36, 37, 38.

If the second rod part 9 is turned by means of the connecting ring 32 via the cylindrical casing 41 so that the circular spring 34 with its cam 35 is retracted from the orifice 36 and by further turning engages the orifice 37, the middle cam 12 engages with the corresponding link assembly 17 and 18. Both the distal cam 11 and the proximal cam 13 become disengaged from the corresponding link assemblies 14, 15, 16 and 19, 20. In this position the reduced gripping force is determined by the stiffness of the compression spring 6. By further turning the connecting ring 32, by the same angle, the third position is reached, wherein the cam 35 engages the orifice 38 and the proximal cam 13 engages the proximal link assembly 19, 20. Distal cam 11 and middle cam 12 will become disengaged from their respective link assemblies. In this configuration force is applied to the jaws 1, 2 via spring 6 and 7 acting in series. As the stiffness of spring 7 is less than that of spring 6, the resulting gripping force will be correspondingly reduced.

The transfer of the turning movement of the switching ring 32 to the turnable rod part 9, 10 is effected via the cylinder casing 41, which is permanently connected at its ends to the second rod part 9 and connecting ring 32 as well as to the cylindrical casing 42. In order to be able to retract the rod 3 proximally, the cylindrical casing 45 is connected to the rod part 10 adjacent to the distal end of the cylindrical casing 42.

At the distal end of the second rod part 9, there is a central axial hole 44 which accommodates a pin 43 secured centrally in the rod part 8. The rod parts 8 and 9 are secured against relative radial movement by the centring action of the pin 43.

In order to prevent the gripping force from being released and in order to avoid resultant possible operational disturbances, the operating rod 3 shifted distally from the rest position is secured against turning. Thus it is not possible to turn the operating rod 3 during operation of the forceps by turning the connecting ring 32. This is effected by keys 11a, 12a and 13a provided on the operating rod 3. Proximal displacement on the rod 3 will cause any key 11a, 12a, 13a adjacent a cam 11, 12, 13 not engaged by a link assembly to engage an aperture 22 in an adjacent link assembly plate 16, 18, 20. The rods is thereby secured against turning.

In order to guarantee the reliability and functional efficiency of the forceps designed according to the invention, the sleeves 14, 17 and 19 should advantageously be secured against turning, for example, by means of a peg engaging an axially extending groove at all times. Furthermore the three link assemblies should be permanently fixed to one another, in order to guarantee that the complementarily designed apertures 22 always take up the same position in relation to one another. This is to ensure that the relative twisting of the link assemblies during use is precluded. Such twisting would prevent the forceps operating in the same manner described above.

Having described the invention in detail with reference to the preferred embodiment, it will be apparent that modifications and variations are possible without departing from the scope of the invention defined in the appended claims.

I claim:

1. Forceps comprising:
   a support;
   a pair of jaws mounted on said support, at least one for pivoting relative to the other between respective gripping and disengaging positions thereof;
   an elongated control rod having a longitudinal axis, mounted on said support for axial movement relative thereto, and including a distal first rod part directly connected to said one jaw and a second rod part extending proximally from and being mounted on said support for turning about said axis relative to said first rod part between respective angular positions thereof;
   at least one lever mounted on said support for movement relative thereto between a released and a locked position;
   means for locking said lever in said locked position thereof; and
   adjusting means for operatively connecting said lever with said first rod part for transmitting forces acting on said lever through said first and second rod parts to said one jaw, including
      a plurality of link assemblies interposed between said first and second rod parts, and
      axially spaced angularly offset cams secured to said second rod part for joint turning therewith and selectively engaging different ones of said link assemblies each in different ones of said angular positions of said second rod part to link said second rod part to said first rod part.

2. Forceps according to claim 1 wherein in a first of said angular positions of said second rod part one of said cams engages one of said link assemblies operative to firmly connect said first rod part to said second rod part, and in a second of said angular positions of said second rod part a different one of said cams engages a different link assembly that includes at least one spring and is operative to transfer force from said second rod part to said first rod part via said at least one spring.

3. Forceps according to claim 2 wherein the number of said cams and corresponding ones of said link assemblies corresponds to the number of gripping force settings to be provided by said adjusting means.

4. Forceps according to claim 3 comprising a spring provided between each adjacent two of said link assemblies such that, when said adjusting means is set to the lowest gripping force, all of said springs act together in series.

5. Forceps according to claim 4 wherein said springs have differing stiffnesses.

6. Forceps according to claim 1 wherein said link assemblies include apertures each for allowing free axial passage of a respective one of said cams with respect to its associated link assembly when not engaged therewith.

7. Forceps according to claim 6 wherein said second rod part includes a key associated with each of said cam and associated link assembly combination and wherein said key engages said associated link assembly when said associated cam and link assembly are axially displaced relative to each other to restrain turning of said second rod part.

8. Forceps according to claim 1 further comprising stop means for restraining said link assemblies against proximal movement.

9. Forceps according to claim 1 wherein said control rod has a switching ring at its proximal end provided with a resilient lock for selectively locking said proximal end of said control rod in a plurality of positions each defining a different jaw gripping force.

10. Forceps according to claim 9 wherein said resilient lock includes a circular spring secured by a peg on the said switching ring against turning relative thereto.

11. Forceps according to claim 9 comprising a cylindrical casing operative for effecting turning of said switching ring.

12. Forceps according to claim 1 further comprising a pin that connects said first and second control rod parts for relative longitudinal movement and secures them against radial movement.

13. Forceps according to claim 1 further comprising means for securing said control rod against turning when said control rod is moved distally out of a rest position thereof.

14. Forceps for gripping tissue with a gripping force that is variable in stages, comprising
   a support;
   a pair of jaws mounted on said support, at least one for pivoting relative to the other between respective gripping and disengaging positions thereof;
   an elongated rod having a longitudinal axis, mounted on said support for axial movement relative thereto, and connected to said one jaw for pivoting the same in response to said axial movement;
   at least one lever mounted on said support for movement relative thereto between a released and a locked position;
   means for locking said lever in said locked position thereof; and
   adjusting means for operatively connecting said lever with said rod for transmitting forces acting on said lever through said rod to said one jaw, including
      means for establishing a direct connection between said lever and said rod when a maximum value of said gripping force is desired, and means including at least one spring for forming an indirect connection incorporating said spring between said lever and said rod to the exclusion of said direct connection when a value less than said maximum value is desired for said gripping force.

15. Forceps according to claim 14 further comprising spring means for connecting a proximal part of said rod to said lever.

* * * * *